United States Patent [19]

Dodge et al.

[11] Patent Number: 5,726,167
[45] Date of Patent: Mar. 10, 1998

[54] INHIBITION OF PHOSPHATIDYLINOSITOL 3-KINASE WITH VIRIDIN, DEMETHOXYVIRIDIN, VIRIDIOL, DEMETHOXYVIRIDIOL, VIRONE, WORTMANNOLONE, AND ANALOGS THEREOF

[75] Inventors: Jeffrey A. Dodge, Indianapolis; Masahiko Sato; Chris J. Vlahos, both of Carmel, all of Ind.

[73] Assignee: Eli Lilly and Company, Indianapolis, Ind.

[21] Appl. No.: 805,704

[22] Filed: Feb. 25, 1997

Related U.S. Application Data

[63] Continuation of Ser. No. 134,337, Oct. 12, 1993.

[51] Int. Cl.$^6$ .................................................. A61K 31/34
[52] U.S. Cl. .......................................................... 514/172
[58] Field of Search ........................... 514/310, 468, 514/172

[56] References Cited

PUBLICATIONS

Bonser, et al. Br. J. Pharmacol. vol. 103, 1237–41, 1991.
Maerki, et al. Arzneim.–Forsch. 42(3) 328–33 (Abstract Supplied), 1992.
Bosner, et al., Br. J. Pharmacol. (1991) 103, 1237–41.
Aldridge, D.C., et al., J.Chem.Soc. Perkin Trans. I: 943–945 (1975).
Blight, M.M., et al., J.Chem.Soc. Perkin Trans I: 1317–1322 (1986).
Jones, R.W., et al., Can.J. Microbiol., 33:963–966 (1987).
Bonser, R.W., et al., Br.J.Pharmacol., 103:1237–1241 (1991).
Matter, W.F., et al., Biochem.Biophys.Res.Commun. 186 (2):624–631 (1992).
Shibaswki, R., et al., J.Biol.Chem., 266 (13): 8108–8114 (1991).
Kaplan, D.R. et al., Cell, 50: 1027–1029 (1987).
Valius, M. et al., Cell. 73:321–334 (1993).
Coughlin, S.R., et al., Science, 243: 1191–1194 (1989).
Kimura, K., et al., Ninth Annual Meeting on Oncogenes, Abstract: 203 (1993).
Bonser, et al., Br.J.Pharmacol. 103, 1237–41 (1991).
Kanai, et al., Biochem.Biophys.Res.Commun., 105 (2) 762–8 (Sep. 15, 1993).
Okada, et al., Seikagadku, 64: 1040 (1992).
Merck Index, 11th Ed.
Maerki, et al., Arzneim–Forsch 42 (3) 328–33 (1992).
Plumb, et al., Proc. Annu. Meet. Am. Assoc. Cancer Res., 34: A501 (1993).
Ser. No. 08/111,796, Aug. 25, 1993, Dodge et al.,
Ser. No. 08/112,012, Aug. 25, 1993, Dodge et al.
Ser. No. 08/094,279, Jul. 19, 1993, Bonjouklian, et al.
Ser. No. 08/111,687, Aug. 25, 1993, Bonjouklian, et al.
Grove, J.F., et al., J.Chem.Soc., June: 3803–3811 (1965).
Neidle, S., et al., J.Chem.Soc. Perkin Trans. I: 760–766 (1972).
Lumsden, R.D., et al., Can.J.Mecorbiol., 38:1274–1280 (1992).
Hanson, J.R., et al. J.Chem.Soc. Perkin Trans. I: 1311–1314 (1985).
Kimura, K., et al., Ninth Annual Meeting on Oncogenes, Abstract:203 (1993).

*Primary Examiner*—Robert Gerstl
*Attorney, Agent, or Firm*—Arleen Palmberg; David E. Boone

[57] ABSTRACT

Viridin, viridiol, demethoxyviridin, demethoxyviridiol, virone, and wortmannolone, and analogs thereof, are inhibitors of phosphatidylinositol 3-kinase. The compounds are particularly useful for inhibiting phosphatidylinositol 3-kinase in vertebrates and for treating phosphatidylinositol 3-kinase-dependent conditions, especially neoplasms, restenosis and atherosclerosis, and bone disorders in vertebrates.

29 Claims, No Drawings

INHIBITION OF PHOSPHATIDYLINOSITOL 3-KINASE WITH VIRIDIN, DEMETHOXYVIRIDIN, VIRIDIOL, DEMETHOXYVIRIDIOL, VIRONE, WORTMANNOLONE, AND ANALOGS THEREOF

This application is a continuation of application Ser. No. 08/134,337, filed on Oct. 12, 1993.

TECHNICAL FIELD OF THE INVENTION

The present invention relates to a method of inhibiting cytoplasmic phosphatidylinositol 3-kinase (PI 3-kinase) in a lysed cell, whole cell, tissue preparation, or organism with viridin, demethoxyviridin, viridiol, demethoxyviridiol, virone, or wortmannolone, or an analog of one of the named compounds. Such compounds also can be used to selectively inhibit phosphatidylinositol 3-kinase in vertebrates, particularly humans, and to treat phosphatidylinositol 3-kinase-dependent conditions, particularly neoplasms, in humans.

BACKGROUND OF THE INVENTION

The metabolism of inositol phospholipids is believed to be an essential part of the receptor-mediated signal transduction pathways in response to various hormones and growth factors [see, e.g., Berridge, M. J., et al., *Nature*, 312: 315–321 (1984); Nishizuka, Y., *Science*, 225: 1365–1370 (1984)].

In this signaling pathway, two intracellular second messengers, inositol 1,4,5-trisphosphate and diacylglycerol are generated through the hydrolysis of phosphatidyl 4,5-bisphosphate by phospholipase C. Inositol 1,4,5-trisphosphate releases $Ca^{2+}$ from intracellular $Ca^{2+}$ stores leading to the activation of $Ca^{2+}$/calmodulin-dependent kinase; diacylglycerol activates protein kinase C. Following breakdown, phosphatidylinositol 4,5-bisphosphate is rapidly resynthesized by stepwise phosphorylation of phosphatidylinositol by phosphatidylinositol 4-kinase and phosphatidylinositol-4-phosphate kinase. These 2 kinases appear to play important roles in the production of second messengers (see, e.g., Duell, T. F., U.S. Pat. No. 5,001,064 (1991); Shibasaki, F., et al., *J. Biol. Chem.*, 266 (13): 8108–8114 (1991).

More recently, the existence of another phosphatidylinositol kinase has been identified and associated with certain activated tyrosine kinases [Courtneidge, S. A., et al., *Cell*, 50: 1031–1037 (1987); Kaplan, D. R., et al., *Cell*, 50: 1021–1029 (1987)]. This kinase, identified as phosphatidylinositol 3-kinase, has been found to phosphorylate the 3-position of the inositol ring of phosphatidylinositol (PI) to form phosphatidylinositol 3-phosphate (PI-3P) [Whitman, D., et al., *Nature*, 322: 664–646 (1988).

In addition to PI, this enzyme also can phosphorylate phosphatidylinositol 4-phosphate and phosphatidylinositol 4,5-bisphosphate to produce phosphatidylinositol 3,4-bisphosphate and phosphatidylinositol 3,4,5-trisphosphate ($PIP_3$), respectively [Auger, K. R., et al., *Cell*, 57: 167–175 (1989)].

PI 3-kinase physically associates with tyrosine kinases such as $pp60^{v-src}$, polyoma middle $T/pp60^{c-src}$, platelet-derived growth factor receptor, colony stimulation factor-1 receptor, and insulin receptor (see, e.g., Shibasaki supra), suggesting it has important, but yet undefined roles in signal transduction, mitogenesis, cell transformation, and other cellular events involving protein tyrosine kinases that associate with and activate PI 3-kinase. PI 3-kinase activity also has been identified in association with G-protein receptors in neutrophils and platelets in neutrophils [Traynor-Kaplan, A. E., et al., *Nature* 334: 353–356 (1988); and Mitchell, C. A., et al., *Proc. Nat. Acad. Sci.*, 87: 9396–9400 (1990)]. However, activation of PI 3-kinase in the neutrophil occurs independently of tyrosine phosphorylation [Vlahos, C. J., et al., *FEBS Letters*, 309 (3): 242–248 (1992)].

PI 3-kinase exists as a tightly associated heterodimer of an 85 kDa regulatory subunit and an 110 kDa catalytic subunit, and is found in cellular complexes with almost all ligand-activated growth factor receptors and oncogene protein tyrosine kinases [Cantley, L. C., et al., *Cell*, 64: 281–302 (1991)]. The 85 kDa subunit regulates the ability of the 110 kDa catalytic subunit of PI 3-kinase to interact with growth factor receptors and tyrosine phosphorylated proteins [Margolis, C., *Cell Growth Differ.*, 3: 73–80 (1992)].

Although PI 3-kinase appears to be an important enzyme in signal transduction, with particular implications relative to mitogenesis and the malignant transformation of cells, only a limited number of compounds have been identified as having inhibitory activity against PI 3-kinase [see, e.g., Matter, W. F., et al., *Biochem. Biophys. Res. Commun.*, 186: 624–631 (1992)]. Contrary to the selective PI 3-kinase activity of the compounds used in the methods of the present invention, the bioflavinoid compounds used by Matter, et al., particularly quercetin and certain analogs thereof, inhibit PI 3-kinase and other kinases such as protein kinase C and PI 4-kinase (Matter, et al., supra).

Thus, the present invention provides a method for inhibiting phosphatidylinositol 3-kinase in a lysed cell, whole cell, tissue, or organism with viridin, demethoxyviridin, viridiol, demethoxyviridiol, virone, or wortmannolone, or an analog of one of the named compounds.

The present invention also provides a method for inhibiting phosphatidylinositol 3-kinase in mammals, particularly humans, using one of the named compounds or an analog thereof.

Furthermore, the present invention provides a method for treating phosphatidylinositol 3-kinase-dependent conditions, particularly neoplasms, in mammals.

SUMMARY OF THE INVENTION

The present invention provides a method of inhibiting phosphatidylinositol 3-kinase in a lysed cell, whole cell, tissue, or organism comprising contacting said lysed cell, whole cell, tissue or organism with a compound of formula I, II or III

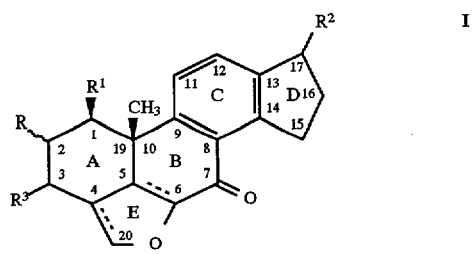

wherein

R is H or methoxy;

$R^1$ is $CH_3$, OH, OAc, $C_1-C_4$ alkoxy or methanesulfonate;

$R^2$ is —OH, —OAc, =O, or —O($C_1-C_4$ alkyl); and $R^3$ is —OH, —OAc, =O, or —O($C_1-C_4$ alkyl), providing no more than two of $R^1$, $R^2$, and $R^3$ can be OAc at the same time;

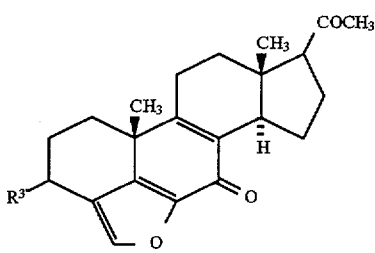

II wherein $R^{3'}$ is =O or —OH; or

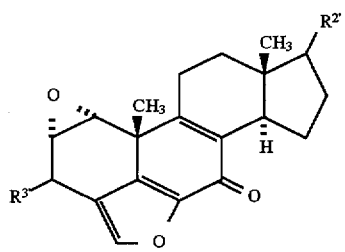

III wherein $R^{2'}$ is =O or —OH; and
$R^{3'}$ is as defined above.

The present invention also provides a method for inhibiting phosphatidylinositol 3-kinase in a vertebrate comprising administering to said vertebrate a phosphatidylinositol 3-kinase inhibiting amount of a compound of formula I, II, or III.

The present invention further provides a method for treating a phosphatidylinositol 3-kinase-dependent condition in a vertebrate in need of such treatment comprising administering to said vertebrate a phosphatidylinositol 3-kinase inhibiting amount of a formula I, II, or III compound.

DETAILED DESCRIPTION OF THE INVENTION

As mentioned above, the present invention relates to a method of inhibiting phosphatidylinositol 3-kinase in a lysed cell, whole cell, tissue, preparation, or organism comprising contacting said whole cell, lysed cell, tissue, or organism with a compound of formula I, II, or III.

The term "$C_1$–$C_4$ alkyl" refers to the straight or branched aliphatic chains of 1 to 4 carbon atoms including methyl, ethyl, propyl, isopropyl, n-butyl, isobutyl, sec-butyl, and tert-butyl (t-butyl).

The designation "OAc" represents acetoxy.

The wavy line at the 2-position of formula I indicates that the 2-position substituent is either in the α- or β-configuration.

In formula I, the dotted line between C-5 and C-6 of the B-ring, and between C-4 and C-20 of the E-ring indicates that a double bond may be present or absent. Generally, formula I compounds are unsaturated at the designated positions. However, C-5 and C-6 are saturated when R is H, $R^2$ is =O and $R^1$ and $R^3$ are OAc (diacetyldemethoxyviridin). C-4 and C-20 are saturated when R is H, $R^1$ is $CH_3$, and $R^2$ and $R^3$ are =O (dehydroxyviridin), and when R is H, $R^1$ is $CH_3$ and $R^2$ and $R^3$ are —OAc (diacetyldemethoxyviridin).

In formulae I, II, and III, the bonds to the respective $R^2$, $R^3$, $R^{2'}$ and $R^{3'}$ substituents are shown to be single bonds. However, one of ordinary skill in the art will recognize that when any one of the identified substituents is oxygen, to form a carbonyl group, a double bond will be present.

Compounds of formulae I, II, and III generally are known in the art. α,β-viridin (formula I in which R is methoxy, $R^1$ is OH, and $R^2$ and $R^3$ are =O) is particularly well known to be biosynthetically produced via the fermentation of any one of a number of strains of the fungus *Gliocladium virens* (erroneously once classified as *Trichoderma viride*) which are readily available to the public [see, e.g., Grove, J. F., et al., *J. Chem. Soc., June:* 3803–3811 (1965); Neidle, S., et al., *J. Chem. Soc. Perkin Trans. II:* 760–766 (1972); Blight, M. M., et al., *J. Chem. Soc. Perkin Trans. I:* 1317–1322 (1986); and Jones, R. W., et al., *Can. J. Microbiol.,* 33: 963–966 (1987)].

During fermentation of one of the above-referenced strains of *Gliocladium virens*, secondary metabolites including viridiol (formula I in which R is methoxy, $R^1$ is OH, $R^2$ is =O, and $R^3$ is OH) and virone (formula II in which $R^{3'}$ is =O) generally are produced. Similarly, wortmannolone (formula III in which $R^{2'}$ is =O and $R^{3'}$ is —OH) is produced by cultivating a readily available culture of *Penicillium wortmanii*. Once produced, each of these compounds may be isolated from the fermentation mixture and purified via known methods (see, e.g., Jones, R. W., et al.; and Blight, M. M., et al., supra).

As previously mentioned, *Gliocladium virens* cultures which produce viridin, viridiol, and virone are readily available to the public. For example, *G. virens* cultures, having the following accession numbers, ATCC 9645 (G-21), ATCC 10043, ATCC 1044 and ATCC 10045, each are available from the American Type Culture Collection (ATCC), 12301 Parklawn Drive, Rockville, Md. 20852; cultures CMI 24039 and CMI 45553 are available from the International Mycological Institute (formerly the Commonwealth Mycological Institute), Baykham Lane, Egham, Surrey, England TW209TY.

Other formula I compounds, demethoxyviridin (in which R is H, $R^1$ is OH, and $R^2$ and $R^3$ are =O) and demethoxyviridiol (in which R is H, $R^1$ is OH, $R^2$ is =O, and $R^3$ is —OH), are produced using procedures which are well known to one of ordinary skill in the art, via fermentation of any one of a number of strains of the fungus *Nodulisporium hinnuleum* and standard isolation and purification techniques [(see, e g., Aldridge, D. C., et al., *J. Chem. Soc. Perkin Trans. I:* 943–945 (1975); Hanson, J. R., et al., *J. Chem. Soc. Perkin Trans. I:* 1311–1314 (1985)].

*Nodulisporium hinnuleum* cultures which biosynthetically produce demethoxyviridin and demethoxyviridiol, having, for example, the following accession numbers, ATCC 24911 (NRRL 6115) and ATCC 36102 (ACC 3199; CMI 214826) also are readily available to the public from the ATCC at the above-stated address.

Wortmannolone, a formula III compound in which $R^{2'}$ is =O and $R^{3'}$ is —OH, is produced by fermenting one of a number of readily available microorganisms of the genus and species *Penicillium wortmannii* klocker (*Taloromyces wortmannii*) such as, for example, CMI 44277.

Once viridin, viridiol, demethoxyviridin, and demethoxyviridiol are isolated and purified, analogs of each may be prepared via well known methods to provide generally known compounds of formula I (see, e.g., Grove, J. F., et al., Hanson, J. R., et al., Aldridge, D. C., et al., and Blight, M. M., et al., supra). Generally, the $R^1$ position hydroxy functionality of each of the above-named formula I compounds may be acetylated, alkylated, oxidized, or dehydrated and alkylated. Similarly, the $R^2$ functionality (=O) of each of the named formula I compounds may be alkylated, or it may be reduced to form an alcohol. The $R^3$ functionality of formula I compounds, when $R^3$ is =O, also may be alkylated to form an acetyl group.

For clarification, Table I below shows the trivial names of representative formula I compounds. However, it is not intended that the invention be limited in scope by reason of any of the following representations.

TABLE 1

Viridin, Viridiol, Demethoxyviridin, Demethoxyviridiol, and Representative Analogs

| | | Functionality | | |
|---|---|---|---|---|
| Trivial Name | R | $R^1$ | $R^2$ | $R^3$ |
| α/β-viridin | α/β-OCH$_3$ | OH | =O | =O |
| 1-acetylviridin | OCH$_3$ | OAc | =O | =O |
| 1-methylether of viridin | OCH$_3$ | OCH$_3$ | =O | =O |
| demethoxyviridin | H | OH | =O | =O |
| demethoxyviridin mono-acetate | H | OAc | =O | =O |
| dehydroxyviridin | H | CH$_3$ | =O | =O |
| demethoxyviridin mono-methanesulfonate | H | OMs | =O | =O |
| diacetyldemethoxyviridol | H | OAc | =O | —OAc |
| viridiol | OCH$_3$ | OH | =O | —OH |
| 1-O-acetylviridiol | OCH$_3$ | OAc | =O | —OH |
| 1-O-methyl-methylether of viridiol | OCH$_3$ | OCH$_3$ | =O | —OH |
| demethoxyviridiol | H | OH | =O | —OH |
| 1-acetyldemethoxyviridiol | H | OAc | =O | —OH |
| 1-O-methylether of dimethoxyviridiol | H | OCH$_3$ | =O | —OH |

In addition, the alcohol of virone (formula II in which $R^{3'}$ is =O) may be prepared via known procedures, and analogs of wortmannolone (formula III in which $R^{2'}$ is =O and $R^{3'}$ is —OH) may be prepared via either reduction of the $R^{2'}$ functionality, oxidation of the $R^{3'}$ functionality, or both, using well known procedures.

In the present method, compounds of formulae I, II, and III are effective for selectively inhibiting phosphatidylinositol 3-kinase in a lysed or whole cell. This method can be carried out in vitro or in vivo and can be utilized as a pharmacological tool for studying, for example, the involvement of PI 3-kinase in mitogenesis, cellular proliferation, or cellular differentiation. The compounds of formulae I, II and III also can be radiolabeled (e.g., tritiated), to provide for easier detection of such compounds in cells.

When a compound of formula I, II, or III is used for this method, such a compound is dissolved in an organic solvent such as dimethylsulfoxide (DMSO), and diluted with HEPES buffer (pH 7.5, containing 15 mM of MgCl$_2$ and 1 mM of EGTA), to the desired concentration. The resulting preparation is then placed in contact with purified PI 3-kinase or a cell according to methods well known in the art.

Another embodiment of the present invention provides a method for inhibiting phosphatidylinositol 3-kinase in a vertebrate, particularly humans, comprising administering to said vertebrate a phosphatidylinositol 3-kinase inhibiting amount of a compound of formula I, II or III.

A preferred embodiment of the present invention includes a method for treating a phosphatidylinositol 3-kinase-dependent condition in a vertebrate comprising administering to said vertebrate a phosphatidylinositol 3-kinase inhibiting amount of a compound of formula I, II, or III. PI 3-kinase-dependent conditions include biochemical processes relevant to pain, diabetes, inflammation, platelet aggregation, vascular diseases such as atherosclerosis and restenosis, bone disorders such as osteoporosis, periodontal disease, bone loss due to steroid or glucocorticoid treatment, Cushing's syndrome, Paget's disease, osteohalisteresis, osteomalacia, hypercalcemia of malignancy, osteopenia due to bone metastases, hyperparathyroidism, rheumatoid or osteoarthritis, and the like, and, particularly, abnormal cell growth as found in neoplasms.

Thus, an especially preferred embodiment of the present invention includes a method of treating phosphatidylinositol 3-kinase-dependent neoplasms, particularly lymphosarcomas, with a compound of formula I, II, or III. Other PI 3-kinase-dependent neoplasms include, for example, adenocarcinoma of the female breast, colon cancer, epidermid cancers of the head and neck, leukemia, melanoma, ovarian carcinoma, plasma cell myeloma, and squamous or small-cell lung cancer.

For therapeutic treatment of the specified indications, a compound of formula I, II, or III may be administered as such, or can be compounded and formulated into pharmaceutical compositions in unit dosage form for parenteral, transdermal, rectal, nasal or intravenous administration or, preferably, oral administration. Such pharmaceutical compositions are prepared in a manner well known in the art and comprise at least one active formula I, II, III compound associated with a pharmaceutical carrier. The term "active compound", as used throughout this specification, refers to at least one formula I, II, or III compound.

In such a composition, the active compound is known as "active ingredients". In making the compositions, the active ingredient usually will be mixed with a carrier, or diluted by a carrier, or enclosed within a carrier which may be in the form of a capsule, sachet, paper or other container. When the carrier serves as a diluent, it may be a solid, semisolid, or liquid material which acts as a vehicle, excipient or medium for the active ingredient. Thus, the composition can be in the form of tablets, pills, powders, lozenges, sachets, cachets, elixirs, emulsions, solutions, syrups, suspensions, soft and hard gelatin capsules, sterile injectable solutions, and sterile packaged powders.

Some examples of suitable carriers, excipients, and diluents include lactose, dextrose, sucrose, sorbitol, mannitol, starches, gum acacia, calcium phosphate, alginates, calcium silicate, microcrystalline cellulose, polyvinylpyrrolidone, cellulose, tragacanth, gelatin, syrup, methyl cellulose, methyl- and propyl-hydroxybenzoates, talc, magnesium stearate, water, and mineral oil. The formulations can additionally include lubricating agents, wetting agents, emulsifying and suspending agents, preserving agents, sweetening agents or flavoring agents. The compositions may be formulated so as to provide quick, sustained, or delayed release of the active ingredient after administration to the patient by employing procedures well known in the art.

For oral administration, a compound can be admixed with carriers and diluents, molded into tablets, or enclosed in gelatin capsules. The mixtures can alternatively be dissolved in liquids such as 10% aqueous glucose solution, isotonic saline, sterile water, or the like, and administered intravenously or by injection.

In the treatment of restenosis the administration of a compound of the invention may be local or systemic delivery. Systemic delivery includes techniques that introduce the compound to the entire organism. Examples of systemic delivery include oral and intravenous administration, previously discussed.

The local delivery of a compound of the invention may be by a variety of techniques which administer the compound at or near the proliferative site. Examples of local delivery techniques are not intended to be limiting but to be illustrative of the techniques available. Examples include local delivery catheters, site specific carriers, implants, or direct injection.

Local delivery by a catheter allows the administration of a pharmaceutical agent directly to the proliferative lesion. Examples of local delivery using a balloon catheter are described in EP 0 383 492 A2 and U.S. Pat. No. 4,636,195 (Wolinsky, 13th Jan. 1987).

Local delivery by an implant describes the surgical placement of a matrix that contains the pharmaceutical agent into the proliferative lesion. The implanted matrix releases the pharmaceutical agent by diffusion, chemical reaction, or solvent activators. Langer, Science 249: 1527–1533 (September 1990). An example of local delivery by an implant is the use of a stent. Stents are designed to mechanically prevent the collapse and reocclusion of the coronary arteries. Incorporating a pharmaceutical agent into the stent delivers the drug directly to the proliferative site. Local delivery by this technique is described in Kohn, *Pharmaceutical Technology* (October 1990). A second example is a delivery system in which a polymer that contains the pharmaceutical agent is injected into the lesion in liquid form. The polymer then cures to form the implant in situ. This technique is described in PCT WO 90/03768 (Donn, 19th Apr. 1990). Another example is the delivery of a pharmaceutical agent by polymeric endoluminal sealing. This technique uses a catheter to apply a polymeric implant to the interior surface of the lumen. The pharmaceutical agent incorporated into the biodegradable polymer implant is thereby released at the surgical site. It is described in PCT WO 90/01969 (Schindler, 23rd Aug. 1989). A final example of local delivery by an implant is by direct injection of vesicles or microparticulates into the proliferative site. These microparticulates may be composed of substances such as proteins, lipids, carbohydrates or synthetic polymers. These microparticulates have the pharmaceutical agent incorporated throughout the microparticle or over the microparticle as a coating. Delivery systems incorporating microparticulates are described in Lange, Science 249: 1527–1533 (September 1990) and Mathiowitz, et al., *J. App. Poly. Sci.*, 26: 809 (1981). Local delivery by site specific carriers describes attaching the pharmaceutical agent to a carrier which will direct or link the drug to the proliferative cells. Examples of this delivery technique includes the use of carriers such as a protein ligand, a monoclonal antibody or a membrane anchored linker. Lange, Science 249: 1527–1533 (September 1990); Langworth, *Genetic Engineering News* (September 1990).

Local delivery by direct injection describes injecting fine particles of the compound suspended in an inert carrier such as sterile saline solution directly into the proliferative region.

The examples of local delivery are merely illustrative and are not mutually exclusive. For example, the delivery of microparticles to the proliferative smooth muscle cells may be by a local delivery catheter or direct injection.

The compositions preferably are formulated in a unit dosage form, each dosage containing from about 1 to about 500 mg and, more frequently, from about 5 to about 300 mg of the active ingredient. The term "unit dosage form" refers to physically discreet units suitable as unitary dosages for human subjects and other vertebrates, each unit containing a predetermined quantity of active material calculated to produce the desired therapeutic effect, in association with the required pharmaceutically acceptable carrier. By "pharmaceutically acceptable", it is meant the carrier, diluent or excipient must be compatible with the other ingredients of the formulation and not deleterious to the recipient thereof.

The following formulation examples are illustrative only and are not intended to limit the scope of the invention in any way. The meaning of the term "active ingredient" is as defined above.

FORMULATION 1

Hard gelatin capsules are prepared using the following ingredients:

|  | Quantity (mg/capsule) |
|---|---|
| Active ingredient | 250 |
| Starch, dried | 200 |
| Magnesium stearate | 10 |
| Total | 460 mg |

FORMULATION 2

A tablet is prepared using the ingredients below:

|  | Quantity (mg/capsule) |
|---|---|
| Active ingredient | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg.

FORMULATION 3

An aerosol solution is prepared containing the following components:

|  | Percent |
|---|---|
| Active ingredient | 0.25 |
| Ethanol | 25.75 |
| Propellant 22 (Chlorodifluoromethane) | 70.00 |
| Total | 100.00 |

The active compound is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

FORMULATION 4

Tablets, each containing 60 mg of active ingredient, are made as follows:

| | Quantity (mg/tablet) |
|---|---|
| Active ingredient | 60 mg |
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch and cellulose are passed through a No. 45 mesh U.S. sieve and mixed thoroughly. The aqueous solution containing polyvinylpyrrolidone is mixed with the resultant powder, and the mixture then is passed through a No. 14 mesh U.S. sieve. The granules so produced are dried at 50° C. and passed through a No. 18 mesh U.S. Sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

FORMULATION 5

Capsules, each containing 80 mg of active ingredient, are made as follows:

| | Quantity (mg/capsule) |
|---|---|
| Active ingredient | 80 mg |
| Starch | 59 mg |
| Microcrystalline cellulose | 59 mg |
| Magnesium stearate | 2 mg |
| Total | 200 mg |

The active ingredient, cellulose, starch, and magnesium stearate are blended, passed through a No. 45 mesh U.S. sieve, and filled into hard gelatin capsules in 200 mg quantities.

FORMULATION 6

Suppositories, each containing 225 mg of active ingredient, are made as follows:

| | Quantity (mg/unit) |
|---|---|
| Active ingredient | 225 mg |
| Saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

FORMULATION 7

Suspensions, each containing 50 mg of active ingredient per 5 ml dose, are made as follows:

| | Quantity |
|---|---|
| Active ingredient(s) | 50 mg |
| Sodium carboxymethyl cellulose | 50 mg |
| Syrup | 1.25 mL |
| Benzoic acid solution | 0.10 mL |
| Flavor | q.v. |
| Color | q.v. |
| Purified water to total | 5 mL |

The active ingredient is passed through a No. 45 mesh U.S. sieve and mixed with the sodium carboxymethyl cellulose and syrup to form a smooth paste. The benzoic acid solution, flavor and color are diluted with a portion of the water and added, with stirring. Sufficient water is then added to produce the required volume.

FORMULATION 8

An intravenous formulation may be prepared as follows:

| | Quantity |
|---|---|
| Active ingredient | 100 mg |
| Isotonic saline | 1,000 mL |

Compounds of formula I are effective against PI 3-kinase and PI 3-kinase-dependent conditions over a wide dosage range. For example, daily dosages will normally fall within the range of about 0.1 mg/kg to about 50 mg/kg of body weight. In the treatment of adult humans, the dosage range from about 5 mg/kg to about 25 mg/kg, in single or divided doses, is preferred. However, it will be understood that the amount of the compound actually administered will be determined by a physician in light of the relevant circumstances including the relative severity of a disease state, the choice of compound to be administered, the age, weight, and response of the individual patient, and the chosen route of administration. Therefore, the above dosage ranges are not intended to limit the scope of this invention in any way.

Compounds of formula I, II and III are active against the PI 3-kinase enzyme. The following is a description of the test systems used to evaluate PI 3-kinase activity.

Purification of Phosphatidylinositol 3-Kinase

Purified PI 3-kinase may be prepared by multiple methods. In one method, PI 3-kinase is prepared-from confluent Swiss 3T3 cells obtained from the American Type Culture Collection, Rockville, Md. Prior to purification of PI 3-kinase, cells are maintained in bulk culture in Dulbecco's Modified Eagles Medium (DMEM; Sigma, St. Louis, Mo.) supplemented with 10% fetal calf serum and are passaged using 0.25% trypsin and 0.02% ethylenediaminetetracetic acid (EDTA). $24 \times 10^6$ cells on four, 100 mm culture plates are washed with 10 mL Hanks Balanced Salt Solution (HBSS; Sigma) pH 7.4, and the cells are left in DMEM without fetal calf serum for 1 hour before being stimulated for 15 minutes with 100 ng/mL of the recombinant human BB homodimer of platelet derived growth factor (PDGF; Genzyme, Cambridge, Mass.). The medium is aspirated and the cells washed with 10 mL of HBSS before being lysed with 3 mL of 137 mM NaCl, 20 mM of Tris (pH 8.0) containing 1 mM of $MgCl_2$, 10% of glycerol, 1% of Triton X-100 (Rohm and Haas, Philadelphia, Pa.), 2 µg/mL of leupeptin, 2 µg/mL of aprotonin, 1 mM or phenylmethylsulfonyl fluoride (PMSF), and 1 mM of sodium orthovanadate. The cells are scraped free from the surface of the dish and centrifuged at 6,000×g for 10 minutes. The supernatant is mixed with 50 µL of washed IgG2bk antiphosphotyrosine antibody beads (Upstate Biotechnology Inc., Lake Placid, N.Y.) in 1.5 mL tubes. The tubes are capped and rotated for 2 hours at 4° C. and the beads are twice washed with 1 mL of HBSS containing 2 µg/mL of leupeptin, 4 µg/mL of aprotonin, 1 mM of PMSF, 200 µM of adenosine, and 1 mM of sodium orthovanadate. The tyrosine phosphorylated PI 3-kinase is eluted from the beads with 200 µL/tube of 10 mM Tris (pH 7.5), 2M of NaCl, 1 mM of EDTA, 200 µM of adenosine, and 10 mM of sodium phenylphosphate.

In another, preferred, method, PI 3-kinase was prepared from bovine brain. Two bovine brains (wet weight about 900 g) were obtained from a local slaughterhouse within minutes of slaughter, packed on ice, and homogenized within one hour. Brains were trimmed of excess fat and blood vessels and then homogenized using a Tekmar Tissuemizer (Cincinnati, Ohio) at 4° C. in 20 mM of Tris(pH 8.3) containing 250 mM of sucrose, 6 mM of β-mercaptoethanol, 1 µg/ml of leupeptin, 1 µg/ml of pepstatin A, 0.4 mM of PMSF, and 1 mM of $MgCl_2$.

Following centrifugation for 60 minutes at 10,000×g, the pH of the supernatant (about 1200 mL) was lowered to 5.75 using dropwise addition of 1M acetic acid at 4° C. After stirring for an additional 15 minutes at 4° C., the solution was centrifuged for 60 minutes at 13,500×g. The supernatant was discarded. Pellets were resuspended in Buffer A (20 mM of Tris, pH 8.3, containing 6 mM of β-mercaptoethanol, 0.1 mM of ethylene glycol-bis(β-aminoethyl ether) N,N,N',N'-tetraacetic acid (EGTA), 1 µg/mL of leupeptin, 1 µg/mL of pepstatin A, and 1 mM of $MgCl_2$), and loaded onto a Fast Flow Q Sepharose column (300 ml) at a flow rate of 5 mL/minute at 4° C. After loading, the column was washed with 3 volumes of Buffer A containing 0.1M of KCl and the kinase was then eluted with a linear gradient of Buffer A/0.1M KCl to Buffer A/0.6M KCl at 3 mL/minute over 7 volumes.

Fractions were assayed for PI 3-kinase activity using 10 µL of the fraction and phosphatidylinositol as substrate as described below. PI 4-kinase eluted in the breakthrough; PI 3-kinase eluted at approximately 0.3M of KCl. The PI 3-kinase pool was subjected to a 40% ammonium sulfate precipitation. Following centrifugation (60 minutes at 13,500×g), pellets were resuspended in Buffer B (10 mM of potassium phosphate, pH 7.4, containing 6 mM of β-mercaptoethanol, 1 µg/mL of leupeptin, 1 µg/mL of pepstatin A, and 1 mM of $MgCl_2$), and loaded onto a 50 mL hydroxylapatite column (Calbiochem, Inc., La Jolla, Calif.) at 2.5 mL/minute. The column was washed with 150 mL Buffer B until the $A_{280}$ baseline reached zero, and the kinase was then eluted with a linear gradient of 10–320 mM of $KH_2PO_4$ at 1 mL/minute over 450 minutes.

Active fractions were pooled and then loaded at 3 mL/minute onto a MonoS column (8 ml) (Pharmacia, Inc., Piscataway, N.J.) equilibrated in Buffer C (50 mM of MES, pH 6.2, containing 6 mM of β-mercaptoethanol, 0.1 mM of EGTA, 1 µg/mL of leupeptin, 1 µg/mL of pepstatin A, and 1 mM of $MgCl_2$). PI 3-kinase was eluted with a linear gradient of 0–0.4M KCl in Buffer C over 120 minutes. In assaying fractions, two pools of PI 3-kinase activity were routinely found. The bulk of the activity was found in the flow-through, while about 20% of the activity was eluted in the gradient. Although the material in the gradient had considerable PI 4-kinase activity, essentially no PI 4-kinase activity was associated with the PI 3-kinase eluted in the flow-through. Therefore, the MonoS flow-through was concentrated by tangential flow filtration on a Mini-Ultrasette Omega 50K membrane (Filtron, Inc., Northborough, Mass.) and diluted in Buffer C to lower the conductivity. The material was then reloaded onto the MonoS column using the above conditions. The PI 3-kinase bound to the column during the wash and was eluted in the gradient. Two pools of phosphatidylinositol kinase activity were obtained in the gradient; each was assayed for PI 3-kinase and PI 4-kinase activity. Pool I was found to contain 95% PI 3-kinase activity (and 5% PI 4-kinase) while Pool II contained predominantly PI 4-kinase activity.

Pool I from the MonoS column was diluted with Buffer A and chromatographed on MonoQ (1 ml) and eluted with a gradient of 0–0.4M KCl in Buffer A. The final pool was assayed for PI 3-kinase and PI 4-kinase activity. The final product was found to contain greater than 99% PI 3-kinase activity.

Assay of Purified PI-3 Kinase Activity

PI 3-kinase activity was measured as previously described by Matter, W. F., et al., *Biochemical and Biophysical Research Communications*, 186: 624–631 (1992). The inhibitor candidate is initially dissolved in DMSO and then diluted 10-fold with 50 mM of HEPES buffer, pH 7.5, containing 15 mM of $MgCl_2$ and 1 mM of EGTA. Ten microliters of this solution are incubated with purified bovine brain PI 3-kinase (9 µL) and phosphatidylinositol (5 µL of a 2 mg/mL stock solution in 50 mM of HEPES buffer, pH 7.5, containing 1 mM of EGTA). The final reaction mixture contains 0.1–5 ng/mL of inhibitor and 3% of DMSO (v:v). This concentration of DMSO has no effect on PI 3-kinase activity; control reaction mixtures contained 3% of DMSO (v:v) without inhibitor. Reactants are preincubated 10 minutes at ambient temperature and then the enzyme reaction is started upon addition of 1 µL [$\gamma$-$^{32}$P]ATP (2 mCi/mL, 500 µM of stock solution; 0.08 mCi/mL, 20 µM of final concentration; Dupont New England Nuclear, Boston, Mass.). The reaction is allowed to proceed for 10 minutes at ambient temperature with frequent mixing, after which time the reaction is quenched by addition of 40 µL of 1N HCl. Lipids are extracted with addition of 80 µL $CHCl_3$:MeOH (1:1, v:v). The samples are mixed and centrifuged, and the lower organic phase is applied to a silica gel TLC plate (EM Science, Gibbstown, N.J.), which is developed in $CHCl_3$:MeOH:$H_2O$:$NH_4OH$ (45:35:8.5:1.5, v:v). Plates are dried, and the kinase reaction visualized by autoradiography. The phosphatidylinositol 3-monophosphate region is scraped from the plate and quantitated using liquid scintillation spectroscopy with ReadyProtein (Beckman Instruments, Inc., Fullerton, Calif.) used as the scintillation cocktail. The level of inhibition for compounds of formulae I, II, and III are determined as the percentage of [$^{32}$P]-counts per minute compared to controls.

Alternatively, products of the PI 3-kinase reaction are confirmed by HPLC as discussed by Whitman, M., *Nature*, 332: 644–646 (1988). Phospholipids are deacylated in methylamine reagent and separated using a Whatman Partisphere SAX anion exchange column as previously described by Auger, K. R., *Cell*, 57: 167–175 (1989). A Radiomatic Model A-140 Flo-One/Beta on-line radioactivity detector is used to monitor the deacylated [$^{32}$P]-enzyme products; deacylated [$^{3}$H]PI 4-monophosphate is added as an internal standard.

When tested on bovine brain purified PI 3-kinase, viridin was an exceptional inhibitor with one-half maximal inhibition, $IC_{50}$, of 0.85 ng/mL (2.4 nM). Thus, the compounds used in the methods of the present invention, particularly viridin, are potent inhibitors of PI 3-kinase.

We claim:

1. A method of inhibiting phosphatidylinositol 3-kinase in a lysed or whole cell comprising contacting said lysed or whole cell with a compound of formula I, II or III

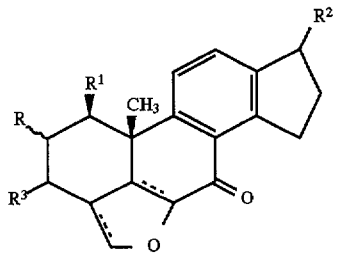

wherein

R is H or methoxy;

$R^1$ is $CH_3$, OH, OAc, $C_1$-$C_4$ alkoxy or methanesulfonate;

$R^2$ is —OH, —OAc, =O, or —O($C_1$-$C_4$ alkyl); and $R^3$ is —OH, —OAc, =O, or —O($C_1$-$C_4$ alkyl), providing no more than two of $R^1$, $R^2$, and $R^3$ can be OAc at the same time;

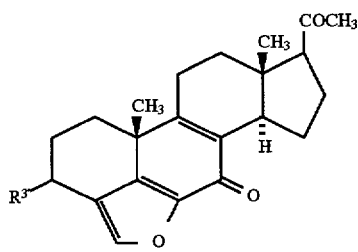

wherein $R^{3'}$ is =O or —OH; or

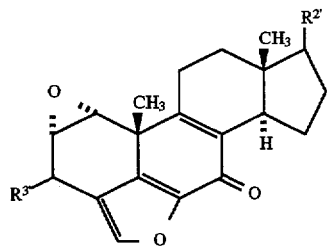

wherein $R^{2'}$ is =O or —OH; and $R^{3'}$ is as defined above.

2. The method of claim 1 wherein said compound is a compound of formula I

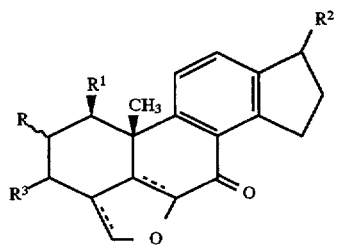

wherein R, $R^1$, $R^2$ and $R^3$ are as defined above.

3. The method of claim 2 wherein R is methoxy, $R^1$ is OH, $R^2$ is =O, and $R^3$ is =O.

4. The method of claim 2 wherein R is H, $R^1$ is OH, $R^2$ is =O, and $R^3$ is =O.

5. The method of claim 2 wherein R is methoxy, $R^1$ is OH, $R^2$ is =O, and $R^3$ is —OH.

6. The method of claim 2 wherein R is H, $R^1$ is OH, $R^2$ is =O, and $R^3$ is —OH.

7. The method of claim 1 wherein said compound is a compound of formula II.

8. The method of claim 7 wherein $R^{3'}$ is =O.

9. The method of claim 1 wherein said compound is a compound of formula III.

10. The method of claim 9 wherein $R^{2'}$ is =O and $R^{3'}$ is —OH.

11. A method for inhibiting phosphatidylinositol 3-kinase in a vertebrate comprising administering to said vertebrate a phosphatidylinositol 3-kinase inhibiting amount of a compound of formula I, II, or III

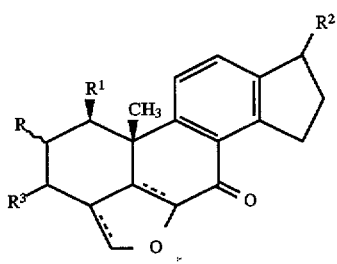

wherein

R is H or methoxy;

$R^1$ is $CH_3$, OH, OAc, $C_1$-$C_4$ alkoxy or methanesulfonate;

$R^2$ is —OH, —OAc, =O, or —O($C_1$-$C_4$ alkyl); and $R^3$ is —OH, —OAc, =O, or —O($C_1$-$C_4$ alkyl), providing no more than two of $R^1$, $R^2$, and $R^3$ can be OAc at the same time;

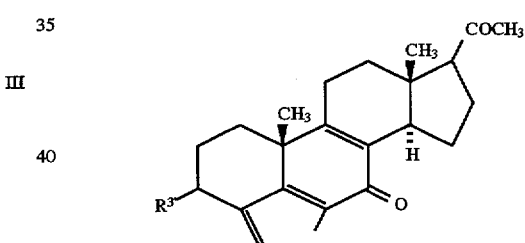

wherein $R^{3'}$ is =O or —OH; or

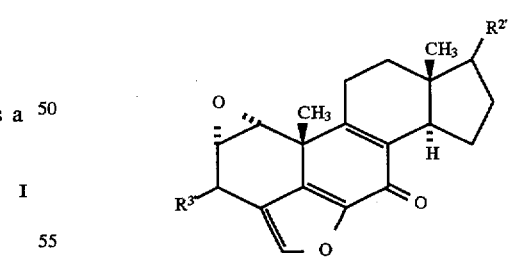

wherein $R^{2'}$ is =O or —OH; and $R^{3'}$ is as defined above.

12. The method of claim 11 wherein said compound is a compound of formula I.

13. The method of claim 12 wherein R is methoxy, $R^1$ is OH, $R^2$ is =O, and $R^3$ is =O.

14. The method of claim 12 wherein R is H, $R^1$ is OH, $R^2$ is =O, and $R^3$ is =O.

15. The method of claim 12 wherein R is methoxy, $R^1$ is OH, $R^2$ is =O, and $R^3$ is —OH.

16. The method of claim 12 wherein R is H, R¹ is OH, R² is =O, and R³ is —OH.

17. The method of claim 11 wherein said compound is a compound of formula II.

18. The method of claim 11 wherein said compound is a compound of formula III.

19. A method for treating a phosphatidylinositol 3-kinase-dependent condition in a mammal in need of such treatment comprising administering to said mammal a phosphatidylinositol 3-kinase inhibiting amount of a compound of formula I, II, or III

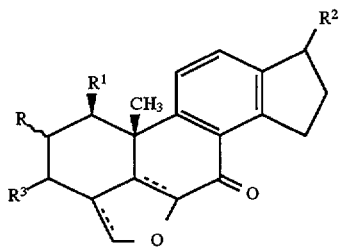

wherein

R is H or methoxy;

R¹ is $CH_3$, OH, OAc, $C_1$-$C_4$ alkoxy or methanesulfonate;

R² is —OH, —OAc, =O, or —O($C_1$-$C_4$ alkyl); and

R³ is —OH, —OAc, =O, or —O($C_1$-$C_4$ alkyl), providing no more than two of R¹, R², and R³ can be OAc at the same time;

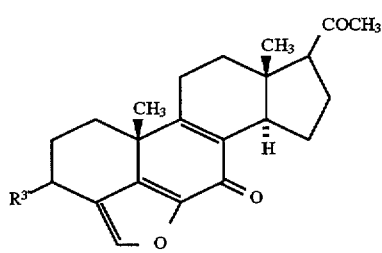

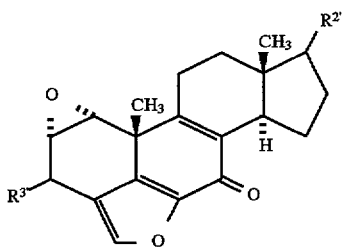

wherein $R^{3'}$ is =O or —OH; or wherein $R^{2'}$ is =O or —OH; and $R^{3'}$ is as defined above.

20. The method of claim 19 wherein said phosphtidylinositol 3-kinase-dependent condition is a neoplasm.

21. The method of claim 19 wherein said phosphatidylinositol 3-kinase-dependent condition is a bone disorder comprising osteoporosis, periodontal disease, bone loss due to steroid or glucocorticoid treatment, Cushing's syndrome, Paget's disease, osteohalisteresis, osteomalacia, hypercalcemia of malignancy, osteopenia due to bone metastases, hyperparathyroidism.

22. The method of claim 19 wherein said phosphatidylinositol 3-kinase-dependent condition is restenosis or atherosclerosis.

23. The method of claim 20 wherein said compound is a compound of formula I.

24. The method of claim 23 wherein R is methoxy, R¹ is OH, R² is =O, and R³ is =O.

25. The method of claim 23 wherein R is H, R¹ is OH, R² is =O, and R³ is =O.

26. The method of claim 23 wherein R is methoxy, R¹ is OH, R² is =O, and R³ is —OH.

27. The method of claim 23 wherein R is H, R¹ is OH, R² is =O, and R³ is —OH.

28. The method of claim 20 wherein said compound is a compound of formula II.

29. The method of claim 20 wherein said compound is a compound of formula III.

* * * * *